US00RE40000E

(19) United States
(12) Reissued Patent
Lukas-Laskey et al.

(10) Patent Number: US RE40,000 E
(45) **Date of Reissued Patent: *Jan. 8, 2008**

(54) METHOD OF TREATMENT FOR DECREASING MORTALITY RESULTING FROM CONGESTIVE HEART FAILURE

(75) Inventors: Mary Ann Lukas-Laskey, Rosemont, PA (US); Robert Ruffolo, Jr., Spring City, PA (US); Neil Howard Shusterman, Wynnewood, PA (US); Gisbert Sponer, Laudenbach (DE); Klaus Strein, Hemsbach (DE)

(73) Assignee: SB Pharmco Puerto Rico Inc., Hato Rey, PR (US)

( * ) Notice: This patent is subject to a terminal disclaimer.

(21) Appl. No.: 10/721,020

(22) Filed: Nov. 25, 2003

Related U.S. Patent Documents

Reissue of:
(64) Patent No.: 5,760,069
Issued: Jun. 2, 1998
Appl. No.: 08/483,635
Filed: Jun. 7, 1995

(30) Foreign Application Priority Data

Feb. 8, 1995 (DE) ..... 19503.995

(51) Int. Cl.
*A61K 31/40* (2006.01)
*A61K 31/585* (2006.01)
*A61K 31/54* (2006.01)
*A61K 31/41* (2006.01)
*A61K 31/34* (2006.01)

(52) U.S. Cl. ..... 514/411; 514/175; 514/223.2; 514/223.5; 514/381; 514/423; 514/471

(58) Field of Classification Search ..... 514/411, 514/175, 223.2, 223.5, 423, 471
See application file for complete search history.

(56) References Cited

U.S. PATENT DOCUMENTS

| | | | | |
|---|---|---|---|---|
| 4,503,067 A | | 3/1985 | Wiedemann et al. | |
| 4,888,179 A | * | 12/1989 | Appelgren et al. | 424/480 |
| 5,308,862 A | * | 5/1994 | Ohlstein | 514/411 |
| 5,312,828 A | * | 5/1994 | Finkelstein et al. | 514/381 |
| 5,760,069 A | * | 6/1998 | Lukas-Laskey et al. | 514/411 |
| 5,902,821 A | * | 5/1999 | Lukas-Laskey et al. | 514/411 |

FOREIGN PATENT DOCUMENTS

| | | |
|---|---|---|
| CA | 1259071 | 9/1989 |
| DE | 696 02 424 T2 | 11/1997 |
| EP | 0 808 162 B1 | 11/1997 |

OTHER PUBLICATIONS

*Bristol Meyers Squib* v. *Ben Venue Labs.*,246 F .3d 1368 (Fed. Cir. 2001).
*Rapoport* v. *Dement*, 254 F.3d 1053 (Fed. Cir.2001).
*Jansen* v. *Rexall Sundown, Inc.*,342 F.3d 1329, 1333–34 (Fed. Cir. 2003).
*Glaxo Group Ltd.* v. *Teva Pharma, Inc.*, 2004 U.S. Dist. LEXIS 16750, at *56–57 (D. Del. 2004).
Swedberg, Karl et al., "Prolongation of Survival in Congestive Cardiomyopathy by Beta–Receptor Blockade," Lancet 1374–1376 (Jun. 30, 1979).
Prichard, B.N.C. and Tomlinson, B., "Choice of Antihypertensive Drug Therapy," Am Heart J; 114 (4): 1030–40 (Oct. 1987).
Das Gupta et al., "Improvement in congestive heart failure following chronic therapy with a new vasodilating betablocker Carvedilol," Circulation, vol. 80, No. 4, Suppl. 2, II –117 (1989).

(Continued)

*Primary Examiner*—Kevin E. Weddington
(74) *Attorney, Agent, or Firm*—Finnegan, Henderson, Farabow, Garrett & Dunner, L.L.P.

(57) ABSTRACT

A method of treatment using a compound of Formula I:

(I)

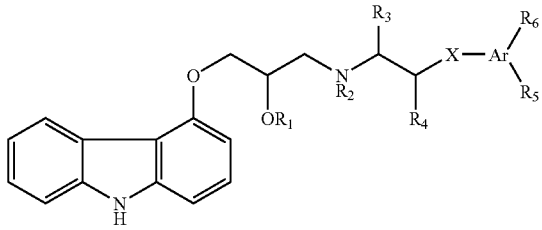

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronapthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

or a pharmaceutically acceptable salt thereof, alone or in conjunction with one or more other therapeutic agents, said agents being selected from the group consisting of ACE inhibitors, diuretics, and digoxin for decreasing mortality resulting from congestive heart failure (CHF) in mammals, particularly humans.

9 Claims, No Drawings

OTHER PUBLICATIONS

DiBanco, Robert et al., "A Comparison of Oral Milrinone, Digoxin, and Their Combination in the Treatment of Patients with Chronic Heart Failure," New England J. Med., vol. 320, No. 11, 677–683 (Mar. 16, 1989).
Das Gupta, P. et al., "Value of carvedilol in congestive heart failure secondary to coronary artery disease," American Journal of Cardiology, vol. 66, No. 15, pp. 1118–1123, (Nov. 1, 1990).
Krukemyer, J., "Use of Beta–Adrenergic Blocking Agents in Congestive Heart Failure," Clin Pharm 9(11): 853–63 (Nov. 1990).
Strein, K. and Sponer, G, "Experimental and clinical pharmacology of carvedilol and other drugs combining vasodilation and beta–adrenoceptor antagonism in a single molecule," Z Kardiol 79 Suppl. 3, pp. 89–98 (1990).
Das Gupta, P. et al., "The effects of intravenous carvedilol, a new multiple action vasodilatory beta–blocker, in congestive heart failure.," J Cardiovasc Pharmacol, vol. 18, Suppl. 7, pp. S 12–16 (1991).
Di Lenarda, Andrea, "Acute Hemodynamic Effects of Carvedilol Versus Metoprolol in Idiopathic Dilated Cardiomyopathy.," Abstract —JACC vol. 17(2), 142A (Feb. 1991).
Hamburger, S.A. et al., "Carvedilol (Kredex®) reduces infarct size in a canine model of acute myocardial infarction," Pharmacology, vol. 43, pp. 113–120 (1991).
Ruffolo, R. et al., "Carvedilol (Kredex®): A Novel Multiple Action Cardiovascular Agent," Drugs of Today 27(7): 465–492 (1991).
Bristow, M.R. et al., "Effects of carvedilol on adrenergic receptor pharmacology in human ventricular myocardium and lymphocytes," Clinical Investig 70 Suppl 1: S105–13 (1992).
Das Gupta, P. et al., "Can intravenous beta–blockade predict long–term hemodynamic benefit in chronic congestive heart failure secondary to ischemic heart disease?" J. Cardiovasc Pharmacol, vol. 19, Suppl. I, pp. S62–7 (1992).
De Cree, J. et al., "Comparative cardiac haemodynamics of bisoprolol, celiprolol, carvedilol and nebivolol in normal volunteers," Int J Clin Pharmacol Res., vol. 12, No. 4, pp. 159–163 (1992).
Feuerstein, G.Z. et al., "Myocardial protection with Carvedilol," J Cardiovasc Pharmacol, vol. 19, Suppl. 1, pp. S138–41 (1992).
Senior, R.; Müller–Beckmann, B., Das Gupta, P., van der Does, R. and Lahiri, A. "Effects of carvedilol on ventricular arrhythmias," J Cardiovasc Pharmacol 19 Suppl. 1:S117–21 (1992).
Sponer, G. et al., "Vasodilatory action of Carvedilol," J Cardiovasc Pharmacol 19 Suppl 1:S5–11 (1992).
Bristow, M.R., "Pathophysiologic and Pharmacologic Rationales for Clinical Management of Chronic Heart Failure with Beta–Blocking Agents," Am J Cardiol 71(9):12C–22C (1993).
Cheng, H.–Y., et al., "Physical chemical investigation of antioxidant properties of carvedilol a cadioprotective drug," International Congress Series No. 1058, Frontiers of reactive oxygen species in biology and medicine, 349–350 (1994).
Feuerstein, G.Z. et al., "Myocardiol protection by the novel vasodilating beta–blocker, carvedilol: potential relevance of anti–oxidant activity," J Hypertens, vol. 11, No. Suppl. 4, pp. S41–8 (Jun. 1993).
Fowler, M.B., "Controlled trials with beta blockers in heart failure: metoprolol as the prototype," Am J Cardiol vol. 71, No. 9, pp. 45C–53C (Mar. 25, 1993).
Kelly, David T., "Carvedilol in Heart Failure," Cardiology 82(suppl 3):45–49 (1993).
Krum, Henry et al., "Controlled Clinical Trials in Heart Failure I: Beta–Blockers," JACC vol. 21, No. 2: 114A, Abstract 725–1 (Feb. 1993).
Lessem, J. N. and Lukas, M.A., "Development of a multiaction beta blocker. Scientific challenges and regulatory needs," Cardiology vol. 82, Suppl 3, pp. 50–58 (1993).
McTavish, Donna, et al., "Carvedilol: A Review of its Pharmacodynamic and Pharmacokinetic Properties, and Therapeutic Efficacy," Drugs, vol. 45, No. 2, pp. 232–258 (Feb. 1993).
Ohlstein, E.H. et al., "Carvedilol, a cardiovascular drug, prevents vascular smooth muscle cell proliferation, migration, and neointimal formation following vascular injury," Proc Natl. Acad. Sci U.S.A., vol. 90, No. 13, pp. 6189–6193 (Jul. 1993).
Olsen, Stephanie et al., "Controlled Clinical Trials in Heart Failure I: Beta Blockers," JACC vol. 21, No. 2:141A, Abstract 725–2 (Feb. 1993).
Metra, M. et al., "Effects of acute and chronic Carvedilol on resting and exercise hemodynamics of patients with idiopathic cardiomyopathy," JACC vol. 21, No. 2:141A, Abstract 725–3 (Feb. 1993).
Rosendorff, C., "Beta–blocking agents with vasodilator activity," J Hypertens Suppl vol. 11, No. 4, pp. S37–40 (Jun. 1993).
Ruffolo, R.R. et al., "Preclinical and clinical pharmacology of Carvedilol," J Hum Hypertens vol. 7 Suppl. 1, pp. S2–15 (Feb. 1993).
Waagstein, Finn, "Beneficial Effects of metoprolol in idiopathic dilated cardiomyopathy," Lancet, vol. 342. 1441–46 (Dec. 11, 1993).
Unknown, "SB to file seven NDAs, launch Havrix hepatitis A vaccine in 1995; No major drugs come off patent through 2000: Genomics work as synergy with diagnostics—BBS," F–C–D Reports—"The Pink Sheet" , vol. 56, No. 51, pp. 17–18 (Dec. 19, 1994).
CIBIS Investigators and Committees, "A Randomized Trial of Beta–Blockade in Heart Failure—The Cardiac Insufficiency Bisoprolol Study (CIBIS)," Circulation, vol. 90(4), 1765–1773 (1994).
Doughty, R.N. et al., "Beta–Blockers in Heart Failure: Promising or Proved?" J Am Coll Cardiol 23(3):814–21 (1994).
Hampton, J.R., "Choosing the right beta–blocker. A guide to selction," Drugs 48(4):549–68 (Oct. 1994).
Hjalmarson, Ake et al., "The Role of Beta–Blockers in the Treatment of Cardiomyopathy and Ischaemic Heart Failure," Drugs 47 (Suppl. 4): 31–40 (1994).
Louis, W.J. et al., "A risk–benefit assessment of carvedilol in the treatment of cardiovascular disorders," Drugs Safety 11(2):86–93 (Aug. 1994).
Metra, Marco et al., "Effects of Short– and Long–Term Carvedilol Administration on Rest and Exercise Hemodynamic Variables, Exercise Capacity and Clinical Conditions in Patients with Idiopathic Dilated Cardiomyopathy," J Am Coll Cardiol vol. 24, No. 7 1678–87 (Dec. 1994).
Unknown, "Smithkline Expands Testing of Carvedilol Due to Effectiveness," Wall St. J. (Midwest Ed) 76(82):B7 (1995).

Unknown, "Survival Chance Improved—BBS," Manufacturing Chemist 66(12):13 (Dec. 1995).
Unknown, "Low dose carvedilol trial success," Pharmaceutical Journal 255(6868):719 (Nov. 1995).
Unknown, "SmithKline Beecham COREG (carvedilol) decreases mortality by 67%—BBS," F–D–C Reports — "The Pink Sheet" vol. 57, No. 47: (T & G 14–T & G 15) (Nov. 20, 1995).
Unknown, "Success halts US trials of carvedilol—BBS," Pharmaceutical Journal, vol. 254, No. 6828, p. 216 (Feb. 18, 1995).
Unknown, "SmithKline expands testing on carvedilol due to effectiveness—BBS," Wall Street Journal, vol. 225, No. 28, p. B6 (Feb. 9, 1995).
Unknown, "Smithkline Beecham/Boehringer Mannheim, UK/Germany: Carvedilol marketed," Bulletin International d'Informations (Droit et Pharmacie) No. 10, pp. 82–83 (Oct. 23, 1995).
Unknown, "SmithKline Beecham to stop its placebo controlled trials for carvedilol in the US," European Chemical News vol. 63, No. 1654, p. 23 (Feb. 1995).
Unknown, "Boerhringer Mannheim and SmithKline Beecham strengthen collaboration to market Carvedilol worldwide," Press Release, p. 1 (Oct. 5, 1995).
Unknown, "SmithKline Beecham: unexpected success halts drug trial," Chemistry and Industry (London): No. 4, p. 123 (Feb. 20, 1995).
Green, Daniel, "UK Company News: SB heart drug proves effective," Financial Times, p. 26 (Feb. 9, 1995).
Australia–New Zealand Heart Failure Research Collaborative Group, "Effects of carvedilol, a vasodilator–beta blocker, in patients with congestive heart failure due to ischemic heart disease," Circulation vol. 92, No. 2, pp. 212–218 (Jul. 15, 1995).
Colucci, W.S. et al., "Carvedilol inhibits clinical progression in patients with mild heart failure—BIO," Circulation, vol. 92, No. 9, Suppl., p. I–395, Abstract 1884 (1995).
Ghali, J.K., "Carvedilol Therapy in Heart Failure—I," J Am Coll Cardiol 26(5):1399 (1995).
Carbajal, E.V., "Carvedilol Therapy in Heart Failure—II," J Am Coll Cardiol 26(5):1399–1400 (1995).
Lee, Y.C., "Carvedilol Therapy in Heart Failure—III," J Am Coll Cardiol 26(5): 1400 (1995).
Olsen, S.L. et al., "Carvedilol Therapy in Heart Failure (Reply)," J Am Coll Cardiol 26(5):1400–1 (1995).
Feuerstein et al., "Carvedilol update III: Rationale for use in congestive heart failure," Drugs of Today, vol. 31 (Suppl. F), pp. 1–23 (Feb. 1995).
Krum, Henry et al., "Double–Blind, Placebo–Controlled Study of the Long–Term Efficacy of Carvedilol in Patients With Severe Chronic Heart Failure," Circulation 92(6): 1499–1506 (Sep. 15, 1995).
Lahiri, A. et al., "Reduction of adverse cardiac events by carvedilol after acute myocardial infarction," European Heart Journal 16(Abstr.Suppl.), p. 36, Abstract P306 (1995).
Olsen, S.L. et al., "Carvedilol Improves Left Ventricular Function and Symptoms in Chronic Heart Failure: A Double–Blind Randomized Study," J Am Coll Cardiol 25(6):1225–31 (May 1995).
Raftery, E.B., "Vasodilating beta–blockers in heart failure," Eur Heart J 16 Suppl F:32–7; erratum in Eur Heart J 16(10): 1451 (1995).
Sackner–Bernstein, J. and Mancini, D.M., "Rationale for Treatment of Patients with Chronic Heart Failure with Adrenergic Blockade," JAMA vol. 274, No. 18, pp. 1462–1467 (1995).
Tham, T.C.K. et al., "The Dose Dependency of the Alpha– and Beta–Adrenoceptor Antagonist Activity of Carvedilol in Man," Br J Clin Pharmacol 40(1):19–23 (1995).
Welter, E.A. and Semchuk, W.M., "The Role of Beta–Blockers in Congestive Heart Failure," J Can Pharm Hosp 48(6):328–35 (1995).
White, M. et al., "What patient with congestive heart failure respond to beta–blocking agents: A Meta–Analysis," Journal of Heart and Lung Transplantation vol. 14, No. 1, p. S85, Abstract 196 (1995).
Winslow, R., "Experimental SmithKline drug shown to combat congestive heart failure—BBS," Wall Street Journal vol. 226, No. 95, p. B 14 (Nov. 14, 1995).
Bonarjee, V.V. and Dickstein, K., "Novel drugs and current therapeutic approaches in the treatment of heart failure," Drugs 51(3):347–58 (Mar. 1996).
Dracup, K., "Heart failure secondary to left ventricular systolic dysfunction. Therapeutic advances and treatment recommendations," Nurse Pract 21(9):57,58,61,65–68 (Sep. 1996).
Feuerstein, G.Z. and Ruffolo, R.R., "Carvedilol, a novel vasodilating beta–blocker with the potential for cardiovascular organ protection," Eur Heart J 17 Suppl B:24–9 (Apr. 1996).
Krum, H. et al, "Changes in plasma endothelin–I levels reflect clinical response to beta–blockade in chronic heart failure," Am Heart J 131(2):337–41 (Feb. 1996).
Packer, M. et al., "The effect of carvedilol on morbidity and mortality in patients with chronic heart failure. U.S. Carvedilol Heart Failure Study Group," N Engl J Med Med 334(21): 1349–55 (May 23, 1996).
Raftery, E.B. "The preventative effects of vasodilating beta–blockers in cardiovacular disease," Eur Heart J 17 Suppl B:30–8 (Apr. 1996).
Sharpe, N., Beta–blockers in heart failure. Future directions, Eur Heart J 17 Suppl B:39–42 (Apr. 1996).
Beta–Blocker Evaluation of Survival Trial Investigators, "A Trial of the Beta–Blocker Bucindolol in Patients with Advanced Chronic Heart Failure," New England J. Med. 344(22), 1659–1667 (May 31, 2001).
Ruffolo, R.R., et al., "Cardioprotective Potential of Carvedilol," Cardiology, 82(suppl 3), 24–28 (1993).
Cohn, J.N., et al., "Effect of Vasodilator Therapy on Mortality in Chronic Congestive Heart Failure," New England J. Med, 314(24), 1547–52 (Jun. 12, 1986).
Whitfield, H.N., et al., "The effect of adrenergic blocking drugs on outflow resistance," Brit. J. Urology, 47, 823–827 (1976).
Caine, M., et al., "The Use of Alpha–adrenergic blockers in Benign Prostatic Obstruction," Brit. J. Urology, 48, 255–263 (1976).
Buchwald, A., et al., Z. Kardiol, 79, 424–28 (1990).
Tepper, D., "Multicenter Oral Carvedilol Heart Failure Assessment (MOCHA)," Frontiers in CHF, 2(1), 39–40 (1996).
Waagstein, F., et al., "Effect of chronic beta–adrenergic receptor blockade in congestive cardiomyopathy," Brit. Heart J., 37, 1022–36 (1975).
Waagstein F. et al., "Beta–blockers in dilated cardiomyopathies: they work," Eur. Heart J., 4(Supp A), 173–78 (1983).

Novopharm, Notice of Allegation and Detailed Statement—Carvedilol 3.125 mg, 6.25 mg, 12.5 mg, and 25 mg Tablets (Nov. 28, 2001).

Notice of Application, *Hoffmann–La Roche Ltd and Smithkline Beecham Corp.* v. *Minister of Health and Novopharm Ltd.*, Court No. T–84–02, Federal Court, Trial Division (Canada) (Jan. 16, 2002).

Pharmascience, Notice of Allegation regarding carvedilol, 3.125 mg, 6.25 mg, 12.5 mg, and 25 mg (Aug. 30, 2001).

Notice of Application, *GlaxoSmithKline Inc. and SmithKline Beecham Corp.* v. *Minister of Health and Pharmascience Inc.*, Court No. T–1871–01, Federal Court, Trial Division (Canada) (Oct. 18, 2001).

Reasons for Order and Order, *GlaxoSmithKline Inc. and SmithKline Beecham Corp.* v. *Minister of Health and Pharmascience Inc.*, Court No. T–1871–01, Federal Court, Trial Division (Canada) (Jul. 18, 2003).

Apotex Inc., Notice of Allegation in respect to Canadian Letters Patent No. 2,212,548 (Jun. 19, 2003).

Swedberg, K., et al., "Beneficial effects of long–term beta–blockade in congestive cardiomyopathy," Brit Heart J., 44, 117–33 (1980).

Swedberg, K., et al., "Adverse effects of beta–blockade withdrawal in patients with congestive cardiomyopathy," Brit. Heart J., 44, 134–42 (1980).

Drexler, H. et al., Characterization of skeletal muscle β–adrenergic receptors in patients with chronic heart failure, Circulation 80(4), II–116 (1989).

Diehm, C., Antihypertensive therapy in arterial occlusive disease, Vasa Suppl, 33, 71–4 (1991) (English language abstract only).

Sponer, G., et al., "Pharmacological profile of β–adrenoceptor blockers with vasodilating properties, especially Carvedilol—rationale for clinical use," Clin. Investig., 70, S20–S26 (1992).

Lessem, J.N., Weber, M.A., "Antihypertensive treatment with a dual–acting beta–blocker in the elderly," J. Hypertens Suppl., 11(4), S29–36 (1993) (Abstract only).

Olsen, S.L., et al., "β–Blocker related improvement in submaximal exercise tolerance in heart failure from idiopathic dilated cardiomyopathy (IDC)", JACC, 19, 146A, Abstract 747–5 (Mar. 1, 1992).

Harder S., et al., "Lack of pharmacokinetic interaction between carvedilol and digitoxin or phenprocoumon," Eur. J. Clin. Pharmacol, 44(6), 583–6 (1993) (Abstract only).

Bristow, M.R., et al., "The β–blocking agents metopolol and Carvedilol affect cardiac adrenergic drive differently in subjects with heart failure from idiopathic dilated cardiomyopathy," JACC, 21(2), 314A (Feb. 1993) (Abstract only).

Australia/New Zealand Heart Failure Research Collaborative Group, "Randomised, placebo–controlled trial of Carvedilol in patients with congestive heart failure due to ischaemic heart disease," Lancet, 349, 375–80 (Feb. 8, 1997).

Teva, Patent Certification Notice Letter re U.S. Patent Nos. 5, 760,069 and 5,902,821 (May 24, 2002).

Packer, M., "Effect of Carvedilol on Survival in Severe Chronic Heart Failure," New England J. Med., 344(22), 1651–1658 (May 31, 2001).

Judgment, German Federal Republic Judgment nullity action 3 Ni 44/00 relating to DE 696 02 424 (EP 0 808 162), *Egis Gyogyszergyar RT* v. *F. Hoffmann–La Rocha AG* (Sep. 18, 2001) (English language translation).

Defendant's Answer to Summons of Jul. 6, 2001, German Federal Republic nullity action 3 Ni 44/00 relating to DE 696 02 424 (EP 0 808 162), *Egis Gyogyszergyar RT* v. *Hoffmann–La Roche AG* (Aug. 23, 2001) (English language translation).

Plaintiff's Brief, German Federal Republic nullity action 3 Ni 44/00 relating to DE 696 02 424 (EP 0 808 162), *Egis Gyogyszergyar RT* v. *Boeringer Hoofmann–La Roche AG* (Aug. 7, 2001) (English language translation).

Substantiation of Opposition of Sep. 21, 2000, German Federal Republic nullity action 3 Ni 44/00 relating to DE 696 02 424 (EP 0 808 162), *Egis Gyogyszergyar RT* v. *Boehringer Hoffmann–La Roche AG* (Dec. 8, 2000) (English language translation).

Nullification Petition, German Federal Republic nullity action relating to DE 696 02 424 (EP 0 808 162), *Egis Gyogyszergyar RT* v. *Boehringer Hoffmann–La Roche AG* (Aug. 4, 2000) (English language translation).

Judgment, German Federal Republic Judgment nullity action 3 Ni 57/91 relating to DE 36 12 537 (Oct. 27, 1992) (English language translation).

Ruling, German Federal Republic, Federal Patent Court, concerning Patent 22 23 237 (Jan. 13, 1989) (English Language Translation).

Official Action, German Patent Office, Application No. P. 195 03 995.5–41 (Aug. 17, 1995).

Official Action, German Patent Office, Application No. P. 195 03 995.5–41 (Nov. 7, 1995).

Affidavit of Dr. William T. Abraham (Mar. 8, 2002), filed in *Hoffmann–La Roche Ltd and Smithkline Beecham Corp.* v. *Minister of Health and Novopharm Ltd.*, Court No. T–84–02, Federal Court, Trial Division (Canada), further including: Exhibit A: Curriculum Vitae of Dr. William T. Abraham, Exhibit B: Novopharm, Notice of Allegation and Detailed Statement—Carvedilol 3.125 mg, 6.25 mg, 12.5 mg, and 25 mg Tablets (Nov. 28, 2001), Exhibit C: Canadian Patent No. 2,212,548, Exhibit D: Glossary of Terms, and Exhibit E: Commentary of Remaining Prior Art in Appendices A & B of the Novopharm Notice of Allegation.

Affidavit of Dr. Mark Lautens (Mar. 8, 2002), filed in *Hoffmann–La Roche Ltd and Smithkline Beecham Corp.* v. *Minister of Health and Novopharm Ltd.*, Court No. T–84–02, Federal Court, Trial Division (Canada), further including: Exhibit A: Curriculum Vitae of Dr. Mark Lautens, Exhibit B: Novopharm, Notice of Allegation and Detailed Statement—Carvedilol 3.125 mg, 6.25 mg, 12.5 mg, and 25 mg Tablets (Nov. 28, 2001), and Exhibit C: Canadian Patent No. 1,259,071.

Affidavit of Edwin J. Gale (Mar. 8, 2002), filed in *Hoffmann–La Roche Ltd and Smithkline Beecham Corp.* v. *Minister of Health and Novopharm Ltd.*, Court No. T–84–02, Federal Court, Trial Division (Canada), further including: Exhibit A: Canadian Patent No. 2,21,548, Exhibit B: Novopharm, Notice of Allegation and Detailed Statement—Carvedilol 3.125 mg, 6.25 mg, 12.5 mg, and 25 mg Tablets (Nov. 28, 2001), Exhibit C: Chart of Claim Types and Allowability in Canada, Exhibit D: Notice concerning acceptable claim types, Canadian Patent Office Record (May 9, 1989), Exhibit E: Canadian Patent Office Manual of Patent Office Practice, §§ 11.10–11.10.02 (Mar. 1998), and Exhibit F: Chart of Claims of Canadian Patent No. 2,212, 548, with claims grouped by type.

Affidavit of Dr. Nadia S. Giannetti (Mar. 8, 2002), filed in *Hoffmann–La Roche Ltd and Smithkline Beecham Corp.* v. *Minister of Health and Novopharm Ltd.*, Court No. T–84–02, Federal Court, Trial Division (Canada), further including: Exhibit 1: Curriculum Vitae of Dr. Nadia S. Giannetti, Exhibit 2: Novopharm, Notice of Allegation and Detailed Statement—Carvedilol 3.125 mg, 6.25 mg, 12.5 mg, and 25 mg Tablets (Nov. 28, 2001), Exhibit 3: Canadian Patent No. 2,212,548, Exhibit 4: Chart of Articles and Patents, Exhibit 5: Letter of Feb. 18, 2002, from Nika V. Ketis, Ph.D., LL.B. (Heenan Blaikie LLP) to Judith Robinson (Ogilvy Renault) regarding Case T–84–02.

Affidavit of Dr. John Parker (Mar. 11, 2002), filed in *Hoffman–La Roche Ltd. and Smithkline Beecham Corp.* v. *Minister of Health and Novopharm Ltd.*, Court No. T–84–02, Federal Court, Trial Division (Canada), further inlcuding: Exhibit A: Curriculum Vitae of Dr. John Parker, Exhibit B: Novopharm, Notice of Allegation and Detailed Statement—Carvedilol 3.125 mg, 6.25 mg, 12.5 mg, and 25 mg Tablets (Nov. 28, 2001), Exhibit C: Canadian Patent No. 2,212,548, Exhibit D: Glossary of Terms, Exhibit E: Packer, M., et al., "The Effect of Carvedilol on Morbidity and Morality in Patients with Chronic Heart Failure," New England J. Med. 334(21), 1349–1355 (May 23, 1996), Exhibit F: Waagstein, F., "Beneficial Effects of Metoprolol in Idiopathic Dilated Cardiomyopathy," Lancet, 342, 1441–1446 (Dec. 11, 1993), Exhibit G: CIBIS Investigators and Committees, "A Randomized Trial of β–Blockade in Heart Failure," Circulation, 90(4), 1765–1773 (Oct. 1994), Exhibit H: Pfeffer, M.A., et al., "β–Adrenergic Blockers and Survival in Heart Failure," New England J. Med. 334(21), 1396–97 (May 23, 1996), Exhibit I: Packer, M., "Effect of Carvedilol on Survival in Severe Chronic Heart Failure," New England J. Med., 344(22), 1651–1658 (May 31, 2001), Exhibit J: Beta–Blocker Evaluation of Survival Trial Investigators, "A Trial of the Beta–Blocker Bucindolol in Patients with Advanced Chronic Heart Failure," New England J. Med. 344(22), 1659–1667 (May 31, 2001) and Exhibit K: Commentary on Remaining Prior Art in Appendices A & B of the Novopharm Notice of Allegation.

Affidavit of Dr. Ian Winterborn (Mar. 11, 2002), filed in *Hoffmann–La Roche Ltd and Smithkline Beecham Corp.* v. *Minister of Health and Novopharm Ltd.*, Court No. T–84–02, Federal Court, Trial Division (Canada), further including Exhibit A: Curriculum Vitae for Dr. Ian Winterborn, Exhibit B: Novopharm, Notice of Allegation and Detailed Statement—Carvedilol 3.125 mg, 6.25 mg, 12.5 mg, and 25 mg Tablets (Nov. 28, 2001), Exhibit C: Notice of Application, *Hoffmann–La Roche Ltd and Smithkline Beecham Corp.* v. *Minister of Health and Novopharm Ltd.*, Court No. T–84–02, Federal Court, Trial Division (Canada) (Jan. 16, 2002), Exhibit D: Canadian Patent No. 2,212,548, Exhibit E: Canadian Patent No. 1,259,071, Exhibit F: Canadian Patent No. 1,129,416, and Exhibit G: United States Patent No. 4,503,067.

Affidavit of Dr. Mary Ann Lukas (Mar. 7, 2002), filed in *Hoffmann–La Roche Ltd and Smithkline Beecham Corp.* v. *Minister of Health and Novopharm Ltd.*, Court No. T–84–02, Federal Court, Trial Division (Canada), further including: Exhibit A: Curriculum Vitae for Dr. Mary Ann Lukas, Exhibit B: Canadian Patent No. 2,212,548, Exhibit C: German Patent Application No. 195 03 995.5 (PCT/EP 96/00498), Exhibit D: English Translation of German Patent Application No. 195 03 995.5 (PCT/EP 96/00498), Exhibit E: U.S. Appl. No. 08/483,635, Exhibit F: Novopharm, Notice of Allegation and Detailed Statement—Carvedilol 3.125 mg, 6.25 mg, 12.5 mg, and 25 mg Tablets (Nov. 28, 2001), Exhibit G: Loeg, H.S., et al., "Effect of Enalapril, Hyralazine Plus Isosorbide Dinitrate, and Prazonsin on Hospitalization in Patients with Chronic Congestive Heart Failure," Circulation 87(6), VI78–VI87 (Jun. 1993), Exhibit H: DiBianco, R., et al., "A Comparison of Oral Milrinone, Digoxin, and Their Combination in the Treatment of Patients with Chronic Heart Failure," New England J. Med., 320(11), 677–683 (Mar. 1989) Exhibit I: Packer, M., et al., "Effect of Oral Milrinone on Mortality in Severe Chronic Heart Failure," New England J. Med. 325(21), 1468–75 (Nov. 21, 1991), Exhibit J: Feldman, A.M., et al., "Effects of Vesnarinone on Morbidity and Mortality in Patients with Heart Failure," New England J. Med., 329(3), 149–155 (Jul. 15, 1993) Exhibit K: Kamoterol in severe heart failure study group, "Xamoterol in Severe Heart Failure," Lancet, 336, 1–6 (Jul. 7, 1990), Exhibit L: Waagstein, F., et al., "Beneficial Effects of Metoprolol in Idiopathic Dilated Cardiomyopathy," Lancet 342, 1441–1446 (Dec. 11, 1993), Exhibit M: CIBIS Investigators and Committees, "A Randomized Trial of β–Blockade in Heart Failure," Circulation, 90(4), 1765–1773 (Oct. 1994), Exhibit N: Packer, M., et al., "The Effect of Carvedilol on Morbidity and Morality in Patients with Chronic Heart Failure," New England J. Med. 334(21), 1349–1355 (May 23, 1996), Exhibit O: Pfeffer, M.A.., et al., "β–Adrenergic Blockers and Survival in Heart Failure," New England J. Med. 334(21), 1396–97 (May 23, 1996), Exhibit P: Packer, M., "Effect of Carvedilol on Survival in Severe Chronic Heart Failure," New England J. Med., 344(22), 1651–1658 (May 31, 2002) and Exhibit Q: Commentary on Remaining Prior Art in Appendices A and B of the Novopharm Notice of Allegation.

Respondent's Record (Pharmascience Inc.) vol. I of III filed in *GlaxoSmithKline Inc., and Smithkline Beecham Corporation* v. *The Minister of Health, and Pharmascience Inc.*, Court File No. T–1871–01 (Canada), containing an index and: Exhibit A: Exhibits to cross–examination of Dr. William T. Abraham taken on Jun. 4, 2002. "77$^{th}$Cardiovascular and Renal Drugs Advisory Committee meeting dated May 2, 1996," pp. 1–356.

Respondent's Record (Pharmascience Inc.) vol. II of III filed in *GlaxoSmithKline Inc., and Smithkline Beecham Corporation* v. *The Minister of Health and Pharmascience Inc.*, Court File No. T–1871–01 (Canada), containing an Index and: Continuation of Exhibit A to Dr. William T. Abraham's cross–examination (pp. 357–572) Exhibit B: Exhibits to cross–examination of Dr. Nadia S. Giannetti taken on Jun. 21, 2002. "Study regarding sauna induced myocardial ischemia in patients with coronary artery disease," pp. 573–578. Exhibit C: Exhibits to cross–examination of Dr. Mary Ann Lukas taken on Jul. 12, 2002. 1) Precise Trial Documentation, pp. 579–752 and 2) CPS Coreg Reference, pp. 753–756.

Respondent's Record (Pharmascience Inc.) vol. III of III filed in *GlaxoSmithKline Inc., and Smithkline Beecham Corporation* v. *The Minister of Health and Pharmascience Inc.*, Court File No. T–1871–01 (Canada), containing an index and: Exhibit D: Memorandum Fact and Law, pp. 755–802. Appendix A ("Anticipation by Kelly" ) to Respondent's Memorandum Fact and Law, pp. 788–801.

Applicant's Record vol. 1 of 6 filed in *GlaxoSmithKline Inc. and Smithkline Beecham Corporation* v. *The Minister of Health Pharmascience Inc.*, Court No. T–1871–00 (Canada), containing an Index and: Exhibit A: Pharmascience Inc. Notice of Allegation dated Aug. 30, 2001, pp. 1–11; Exhibit B: Notice of Application issued Oct. 18, 2001 (Canada, Federal Court–Trial Division, Court No. 1871–01), pp. 12–27; Exhibit C: Pharmascience Inc. Notice of Appearance dated Oct. 26, 2001 (Canada, Federal Court–Trial Division, Court No. 1871–01), pp. 28–31; Exhibit D: Order of Prothonotary Lafreniére dated Dec. 13, 2001 (Canada, Federal Court–Trial Division, Court No. 1871–01), pp. 32–35; Exhibit E: Order of Prothonotary Lafreniére dated Mar. 7, 2002 (Canada, Federal Court–Trial Division, Court No. 1871–01), pp. 36–39; Exhibit F: Order of Prothonotary Lafreniére dated Jun. 11, 2002 (Canada, Federal Court–Trial Division, Court No. 1871–01), pp. 40–44;

Exhibit G: Confidentiality Order of Prothonotary Lafreniére dated Aug. 2, 2002 (Canada, Federal Court–Trial Division, Court No. 1871–01), pp. 45–55; Exhibit H: Affidavit of Dr. William T. Abraham sworn Jan. 29, 2002 (Canada, Federal Court–Trial Division, Court No. 1871–01), pp. 56–96, further including: Exhibit A: *Curriculum vitae*, pp. 97–142; Exhibit B: Notice of Allegation, pp. 143–154; Exhibit C: Canadian Letters Patent No. 2,212,548, pp. 155–186; Exhibit D: Glossary of medical terms, pp. 187–193; Exhibit E: Further commentary on prior art, pp. 194–209; Exhibit I: Transcript of cross–examination of Dr. Abraham taken on Jun. 4, 2002 (Canada, Federal Court–Trial Division, Court No. 1871–01), pp. 210–350, further including Exhibit 1 (Vogel et al., 24 Am. J. Cardiology 198–207 (1969)), Exhibit 2 (Bristow et al., 94 Circulation 2807–2816 (1996)), Exhibit 3 (Gilbert et al., 94 Circulation 2817–2825 (1996)), and Exhibit 4 (Shakar et al., 31 JACC 1336–1340 (1998));

Exhibit J: Affidavit of Dr. Nadia S. Giannetti sworn Jan. 30, 2002 (Canada, Federal Court–Trial Division, Court No. 1871–01), pp. 351–371, further including: Exhibit 1: *Curriculum vitae*, pp. 372–384; Exhibit 2: Notice of Allegation, pp. 385–396; Exhibit 3: Canadian Letters Patent No. 2,212, 548, pp. 397–428; Exhibit 4: List of prior art referenced in Notice of Allegation, pp. 429–438; Exhibit K: Transcript of cross–examination of Dr. Giannetti taken on Jun. 21, 2002 (Canada, Federal Court–Trial Division, Court No. 1871–01), pp. 439–529.

Applicants' Record vol. 2 of 6 filed in *GlaxoSmithKline Inc., and Smithkline Beecham Corporation* v. *The Minister of Health and Pharmascience Inc.*, Court No. T–1871–00 (Canada), containing an Index and: Exhibit L: Affidavit of Patricia N. Jansons sworn Jan. 24, 2002 (Canada, Federal Court–Trial Division, Court No. 1871–01), pp. 530–540, further including: Exhibit A: Certified copy of Canadian Letters Patent No. 1,259,071, pp. 541–583; Exhibit B: Certified copy of the Abstract of Title for Canadian Letters Patent No. 1,259,071, pp. 584–585; Exhibit C: Certified copy of Canadian Letters Patent No. 2,212,548, pp. 586–617; Exhibit D: Certified copy of the Abstract of Title for Canadian Letters Patent No. 2,212,548, pp. 618–619; Exhibit E: Copy of CPS entry for COREG™, pp. 620–625; Exhibit F: Copies of the 76 prior art references listed as paragraphs 1 to 13 and Appendix A of the Notice of Allegation (Tabs 1–46), pp. 626–1022.

Applicants' Record vol. 3 of 6 filed in *GlaxoSmithKline Inc., and Smithkline Beecham Corporation* v. *The Minister of Health and Pharmascience Inc.*, Court No. T–1871–00 (Canada), containing an Index and: Exhibit L (cont.): Exhibit F: Copies of the 76 prior art references listed at paragraphs 1 to 13 and Appendix A of the Notice of Allegation (Tabs 47–76), pp. 1023–1186; Exhibit M: Affidavit of Dr. Mary Ann Lukas sworn Jan. 30, 2002 (Canada, Federal Court–Trial Division, Court No. 1871–01), pp. 1187–1212, further including: Exhibit A: *Curriculum vitae*, pp. 1214–1221, Exhibit B: Canadian Letters Patent No. 2,212,548, pp. 1222–1253; Exhibit C: German Patent Application No. 19503995.5 dated Feb. 8, 1995, pp. 1254–1260; Exhibit D: English translation of German Application, pp. 1261–1267; Exhibit E: U.S. Appl. No. 08/483,635 dated Jun. 7, 1995, pp. 1268–1290; Exhibit F: Notice of Allegation, pp. 1291–1302; Exhibit G: Loeb publication, 1993, pp. 1303–1313;

Exhibit H: DiBianco publication, 1989, pp. 1314–1321; Exhibit I: Packer publication, 1991, pp. 1322–1330; Exhibit J: Feldman publication, 1993, pp. 1331–1338; Exhibit K: Results of Xamoterol Trial, pp. 1339–1345; Exhibit L: Results of Metoprolol in Dilated Cardiomyopathy (MDC) Trial, pp. 1346–1352; Exhibit M: Results of the CIBIS I Trial, pp. 1353–1362; Exhibit N: Results of the U.S. Carvedilol Trials, pp. 1363–1370; Exhibit O: Pfeffer editorial on U.S. Carvedilol Trials, pp. 1371–1373; Exhibit P: Results of COPERNICUS Trial, pp. 1374–1382; Exhibit Q: Further commentary om prior art, pp. 1383–1393.

Applicants' Record vol. 4 of 6 filed in *GlaxoSmithkline Inc., and Smithkline Beecham Corporation* v. *The Minister of Health and Pharmascience Inc.*, Court No. T–871–00 (Canada), containing an Index and: Exhibit N: Transcript of cross–examination of Dr. Lukas taken on Jul. 12, 2002 (Canada, Federal Court–Trial Division, Court No. T–1871–01), pp. 1394–1795, further including Exhibit 1 (SmithKline Beecham Pharm., SK&F 105517/Carvedilol, protocol 220 (Oct. 20, 1993), Exhibit 2 (SmithKline Beecham Pharm., SK&F 105517/Carvedilol, protocol 221 (Oct. 20, 1993)), Exhibit 3 (SmithKline Beecham Pharm., SK&F 105517/Carvedilol, protocol 239 (Jun. 9, 1994)), Exhibit 4 (SmithKline Beecham Pharm., SK&F 105517/Carvedilol, protocol 240 (Jan. 25, 1994)); Exhibit O: Affidavit of Dr. John Parker sworn Jan. 31, 2002 (Canada, Federal Court–Trial Division, Court No. T–1871–01), pp. 1796–1828, further including: Exhibit A: *Curriculum vitae*, pp. 1829–1851;

Exhibit B: Notice of Allegation, pp. 1852–1863; Exhibit C: Canadian Letters Patent No. 2,212,548, pp. 1864–1896; Exhibit D: Glossary of medical terms, pp. 1897–1903; Exhibit E: Results of U.S. Carvedilol Trials, pp. 1904–1910; Exhibit F: Results of Metoprolol in Dilated Cardiomyopathy (MDS) Trials, pp. 1911–1917; Exhibit G: Results of CIBIS I Trial, pp. 1918–1927; Exhibit H: Pfeffer editorial on U.S. Carvedilol Trials, pp. 1928–1930; Exhibit I: Results of COPERNICUS Trial, pp. 1931–1939; Exhibit J: Results of BEST Trial, pp. 1940–1949; Exhibit K: Further commentary in prior art, pp. 1950–1959; Exhibit P: Transcript of cross–examination of Dr. Parker taken on Jul. 3, 2002, pp. 1960–2082.

Applicants' Record vol. 5 of 6 filed in *GlaxoSmithKline Inc., and Smithkline Beecham Corporation* v. *The Minister of Health and Pharmascience Inc.*, Court No. T–1871–00, containing an Index and: Exhibit Q: Affidavit of Dr. Bertram Pitt sworn Apr. 1, 2002 (Canada, Federal Court–Trial Division, Court No. T–1871–01), pp. 2083–2121, further including Exhibit A: *Curriculum vitae,*pp. 2122–2193; Exhibit B: Comparison document prepared by Hitchman & Sprigings, pp. 2194–2209; Exhibit R: Transcript of cross–examination of Dr. Pitt taken on Jun. 24, 2002 (Canada, Federal Court–Trial Division, Court No. T–1871–01), pp. 2210–2284; Exhibit S: Affidavit of Dr. Robert Rangno sworn Apr. 1, 2002 (Canada, Federal Court–Trial Division, Court No. T–1871–01), pp. 2285–2324, further including Exhibit 1: *Curriculum vitae*, pp. 2325–2342; Exhibits 2–4 not included: Documents struck by Canadian Court order dated Jun. 11, 2002

Exhibit T: Transcript of cross–examination of Dr. Rangno taken on Jun. 26, 2002 (Canada, Federal Court–Trial Division, Court No. T–1871–01), pp. 2346–2411; Exhibit U: Affidavit of Patrick Taylor sworn Apr. 2, 2002 (Canada, Federal Court–Trial Division, Court No. T–1871–01), pp. 2412–2414, further including: Exhibit A: Product Monograph for COREG™ (carvedilol), pp. 2415–2419; Exhibit B: Further Detailed Information of the Prior Art References found in Appendix "A" to the Pharmascience notice of Allegation, pp. 2420–2463; Exhibits C–F not included: Documents struck by Canadian Court order dated Jun. 11, 2002; Exhibit V: Affidavit of Dr. Lawrence Zisman sworn Apr. 1, 2002 (Canada, Federal Court–Trial Division, Court No. T–1871–01), pp. 2469–2490, further including Exhibit A: *Curriculum vitae*, pp. 2491–2504; Exhibit B: Comparison document prepared by Hitchman & Sprigings, pp. 2505–2521;

Exhibit W: Transcript of cross–examination of Dr. Zisman taken on Jul. 10, 2002, pp. 2522–2592.

Applicants' Record vol. 6 of 6 filed in *GlaxoSmithKline Inc., and Smithkline Beecham Corporation* v. *The Minister of Health and Pharmascience Inc.*, Court No. T–1871–00, further including: Exhibit X: Written Representations, Applicants' Memorandum of Fact and Law, pp. 2593–2623.

Affidavit of Edwin J. Gale, Mar. 8, 2002, filed in *Hoffmann–La Roche Limited, and Smithkline Beecham Corporation* v. *The Minister of Health, and Novopharm Limited*, Court No. T–84–02, further including: Exhibit A: Copy of Canadian Letters Patent No. 2,212,548; Exhibit B: Notice of Allegation dated Nov. 28, 2001 from Novapharm Limited to Hoffmann–La Roche; Exhibit C: Chart of Edwin J. Gale illustrating various claim types used to cover pharmaceuticals including first and second medical uses and pharmaceuticals: Exhibit D: Practice Notice regarding Chemical Patent Practice from the Canadian Patent Office Record of May 9, 1989; Exhibit E: Copy of section on Method of Use and Use claims from the Canadian Manual of Patent Office Practice dated Mar. 1998; Exhibit F: Copy of Canadian Patent No. 2,212,548 claims grouped by type.

Applicants' Record filed in *GlaxoSmithKline Inc. and Smithkline Beecham Corporation* v. *Apotex Inc. and The Minister of Health*, Court File No. T–2105–02 (Canadian Federal Court–Trial Division), containing an Index and: Exhibit A: Apotex Inc. Notice of Allegation dated Nov. 1, 2003, pp. 1–2; Exhibit B: Notice of Application dated Dec. 16, 2002, pp. 3–13; Exhibit C: Apotex Inc. Notice of Appearance dated Dec. 20, 2002, pp. 14–16; Exhibit D: Minister of Health Notice of Appearance dated Dec. 31, 2002, pp. 17–18; Exhibit E: Affidavit of Lidia O. Derewlany sworn on Feb. 14, 2003, pp. 19–23, further including: Exhibit 1: Canadian Patent No. 2,212,548, pp. 24–54; Exhibit 2: Abstract of title for Canadian Patent No. 2,212, 548, pp. 55–56; Exhibit 3: German Patent Application No. 19503995.5, pp. 57–63; Exhibit 4: English translation of German Patent Application No. 19503995.5, pp. 64–70; Exhibit 5: U.S. Appl. No. 08/483,635, pp. 71–92;

Exhibit 6: Notice of Compliance dated Feb. 17, 1995 and approved product monograph for Kredex tablets, pp. 93–115; Exhibit 7: Cover page of the S/NDS dated Dec. 13, 1995 for Coreg™ tablets (redacted), pp. 116–118; Exhibit 8: Correspondence from Viera Pastorek, Health Canada, dated Jan. 10, 1996, pp. 119–121; Exhibit 9: Notice of Compliance dated Sep. 30, 1996, pp. 122–160; Exhibit 10: Health Canada Patent Lists filed by Hoffman–La Roche for Coreg™ tablets, pp. 161–165; Exhibit 11: Cover page for the Sep. 13, 2001 S/NDS filed by GlaxoSmithKline Inc., pp. 166–167; Exhibit 12: Correspondence from A. Minkiewicz–Janda dated Oct. 29, 2001, pp. 168–171; Exhibit 13: Health Canada Patent Lists filed by GlaxoSmithKline Inc., pp. 172–176; Exhibit 14: Notice of Compliance dated Apr. 10, 2002 and approved product monograph for Coreg™ tablets, pp. 177–227; Exhibit F: Transcript of cross–examination of Lidia O. Derewlany taken Apr. 24, 2003, pp. 229–269;

Exhibit G: Correspondence dated May 23, 2003 for Ogilvy Renault to Goodmans LLP, pp. 270–271; Exhibit H: Affidavit of Dianne Kathleen Grisé sworn on Feb. 14, 2003, pp. 272–275; Exhibit I: Transcript of cross–examination of Dianne Kathleen Grisé taken May 6, 2003, pp. 276–312; Exhibit J: Affidavit of Bernard Sherman sworn on Mar. 7, 2003, pp. 313–315; Exhibit K: Written Representations, memorandum of Fact and Law, of GlaxoSmithKline and SmithKline Beecham Corporation dated Jun. 5, 2003, pp. 316–346.

Applicants' Record, vol. 1 of 7, filed in *Hoffmann–La Roche Limited and Smithkline Beecham Corporation* v. *The Minister of Health and Novopharm Limited*, Court No. T–84–02 (Canadian Federal Court–Trial Division), containing an Index and: Exhibit A: Novopharm Limited Notice of Allegation dated Nov. 28, 2001, pp. 1–20; Exhibit B: Notice of Application issued Jan. 16, 2002, pp. 21–36; Exhibit C: Novopharm Limited Notice of Appearance dated Jan. 18, 2002, pp. 37–39; Exhibit D: Minister of Health Notice of Appearance dated Jan. 24, 2002, pp. 40–41; Exhibit E: Order of Prothonotary Lafreniére dated Feb. 11, 2002, pp. 42–44; Exhibit F: Confidentiality Order of Prothonotary Lafreniére dated Feb. 11, 2002, pp. 45–52; Exhibit G: Correspondence dated Feb. 18, 2002 from Heenan Blaikie, counsel for the Respondent, Novopharm Limited to Ogilvy Renault, counsel for the Applicants, pp. 53–55;

Exhibit H: Order of Prothonotary Lafreniére dated Nov. 4, 2002, pp. 56–57; Exhibit I: Correspondence dated Jan. 27, 2003 from Heenan Blaikie, counsel for the Respondent, Novopharm Limited to Ogilvy Renault, counsel for the Applicants, pp. 53–57a; Exhibit J: Affidavit of Patricia N. Jansons sworn Mar. 4, 2002, pp. 58–72, further including: Exhibit A: Certified copy of Canadian Letters Patent No. 1,259,071, pp. 73–115; Exhibit B: Certified copy of the Abstract of Title for Canadian Letters Patent No. 1,259,071, pp. 116–117; Exhibit C: Certified copy of Canadian Letters Patent No. 2,212,548, pp. 118–146; Exhibit D: Certified copy of the Abstract of Title for Canadian Letters Patent No. 2,212,548, pp. 147–148; Exhibit E: Copy of CPS entry for COREG™, pp. 149–154; Exhibit F: Copies of the 104 prior art references listed at page 5 & 6 and Appendix A & B of the Novopharm Notice of Allegation, pp. 155–534.

Applicants' Record, vol. 3 of 7, filed in *Hoffmann–La Roche Limited, and Smithkline Beecham Corporation* v. *The Minister of Health and Novopharm Limited*, Court No. T–84–02, further including: Exhibit K: Affidavit of Dr. Mary Ann Lukas sworn Mar. 7, 2002, pp. 1026–1059, further including: Exhibit A: *Curriculum vitae*, pp. 1060–1067; Exhibit B: Canadian Letters Patent No. 2,212,548, pp. 1068–1105; Exhibit C: German Patent Application No. 19503995.5 dated Feb. 8, 1995, pp. 1106–1112; Exhibit D: English translation of German Application, pp. 1113–1119; Exhibit E: U.S. Appl. No. 08/483,635 dated Jun. 7, 1995, pp. 1120–1141; Exhibit F: Novopharm Notice of Allegation (Nov. 28, 2001), pp. 1142–1162; Exhibit G: Loeb et al., 87 Circulation VI–78 to VI–87 (1993), pp. 1163–1173; Exhibit H: DiBianco et al., 320 N.E.J. Med. 677–683 (1989), pp. 1174–1181; Exhibit I: Packer et al., 325 N.E.J. Med. 1468–1475 (1991), pp. 1182–1190;

Exhibit J: Feldman et al., 329 N.E.J. Med. 149–155 (1993), 1191–1198; Exhibit K: Results of Xamoterol Trial, 336 Lancet 1–6 (1990), pp. 1199–1205; Exhibit L: Results of the Metoprolol in Dilated Cardiomayopathy (MDS) Trial, 342 Lancet 1441–46 (1993), pp. 1206–1212; Exhibit M: Results of the CIBIS I Trial, 90 Circulation 1765–1773 (1994), pp. 1213–1222; Exhibit N: Results of the U.S. Carvedilol Trials, 334 N.E.J. Med. 1349–1355, pp. 1223–1230; Exhibit O: Pfeffer editorial on U.S. Carvedilol Trials 334 N.E.J. Med. 1396–1397, pp. 1231–1233; Exhibit P: Results of COPERNICUS Trial, 344 N.E.J. Med. 1651–1658, pp. 1234–1242; Exhibit Q: Further commentary on prior art, pp. 1243–1256; Exhibit L: Transcript of cross–examination of Dr. Lukas taken on Jan. 28, 2003, pp. 1257–1333; Exhibit M: Affidavit of Dr. William T. Abraham sworn Mar. 8, 2002, pp. 1334–1382, further including: Exhibt A: *Curriculum vitae*, pp. 1383–1428; Exhibit B: Notice of Allegation (pp. 3–19), pp. 1429–1449;

Exhibit C: Canadian Letters Patent No. 2,212,548, pp. 1450–1481; Exhibit D: Glossary of medical terms, pp. 1482–1488, Exhibit E: Further commentary on prior art, pp. 1489–1506; Exhibit N: Transcript of cross–examination of Dr. Abraham taken on Nov. 26, 2002, pp. 1507–1628, further including: Exhibit 1: Abraham et al., 39 Advances in Internal Medicine, 22–47 (1994); Exhibit 2: Results of CONSENSUS Trial, 316 N.E.J. Med. 1429–1435 (1987); Exhibit 3: Bristow et al., 94 Circulation, 2807–16 (1996); Exhibit 4: Shakar et al., 31 JACC 1336–1340 (1998), Exhibit 5: Gilbert et al., 94 Circulation 2817–25 (1996); Exhibit 6: Abraham et al., 22 Hepatology, 737–743 (1995).

Applicants' Record, vol. 4 of 7, filed in *Hoffmann–La Roche Limited, and Smithkline Beecham Corporation* v. *The Minister of Health, and Novopharm Limited*, Court No. T–84–02, containing an Index and: Exhibit O: Affidavit of Dr. Nadia S. Giannetti sworn Mar. 8, 2002, pp. 1629–1656 further includingg Exhibit 1: *Curriculum vitae*, pp. 1657–1669; Exhibit 2: Novopharm Notice of Allegation (Nov. 28, 2001), pp. 1670–1690; Exhibit 3: Canadian Letters Patent No. 2,212,548, pp. 1691–1723; Exhibit 4: List of prior art referenced in Notice of Allegation, pp. 1724–1737; Exhibit 5: Correspondence from Heenan Blaikie to Ogilvy Renault dated Feb. 18, 2002, pp. 1739–1742; Exhibit P: Transcript of cross–examination of Dr. Giannetti taken on Dec. 20, 2002, pp. 1743–1842, further including Exhibit 1: Johnstone et al., 10 Can. J. Cardiol 613–631 (1994); Exhibit 2: Giannetti et al., 107 Am. J. Med., 228–233 (1999);

Exhibit 3: Cecere et al., Can J Cardiol, vol. 17, Supp C, Abstract 272 (Sep. 2001); Exhibit 4: Cecere et al., Can J Cardiol, vol. 17, Supp C, Abstract 376 (Sep. 2001); Exhibit 5: Cantarovich et al., J. Heart Lung Trans, vol. 20(2), Abstract 246 (2001); Exhibit 6: Cantarovich et al., J. Heart Lung Trans, vol. 20(2), Abstract 166 (2001); Exhibit Q: Affidavit of Dr. Mark Lautens sworn Mar. 8, 2002, pp. 1843–1847, further including Exhibit A: *Curriculum vitae*, pp. 1848–1877; Exhibit B: Novopharm Notice of Allegation (Nov. 28, 2001), pp. 1878–1898; Exhibit C: Canadian Letters Patent No. 1,259,071, pp. 1899–1941; Exhibit R: Affidavit of Edwin Gale sworn Mar. 8, 2002, pp. 1942–1951, further including: Exhibit A: Copy of Canadian Letters Patent No. 2,212,548, pp. 1952–1983; Exhibit B: Novopharm Notice of Allegation (Nov. 28, 2001), pp. 1984–2004; Exhibit C: Chart illustrating various claim types used to cover pharmaceuticals, pp. 2005–2006;

Exhibit D: Practice Notice regarding Chemical Patent Practice taken from the Canadian Patent Office Record of May 9, 1989, pp. 2007–2008; Exhibit E: Section 11.10.02 entitled "Method of Use and Use Claims" from the Canadian Manual of Patent Office Practice, pp. 2009–2013; Exhibit F: Canadian Letters Patent No. 2,212,548 claims grouped by type, pp. 2014–2015.

Applicants' Record, vol. 5 of 7 , filed in *Hoffmann–La Roche Limited, and Smithkline Beecham Corporation* v. *The Minister of Health, and Novopharm Limited*, Court No. T–84–02, containing an Index and: Exhibit S: Affidavit of Dr. John Parker sworn Mar. 11, 2002, pp. 2016–2054, further including: Exhibit A: *Curriculum vitae*, pp. 2055–2077; Exhibit B: Notice of Allegation, pp. 2078–2098; Exhibit C: Canadian Letters Patent No. 2,212, 548, pp. 2099–2130; Exhibit D: Glossary of medical terms, pp. 2131–2137; Exhibit E: Parker et al., 334 N.E.J. Med. 1349–1355 (1996), pp. 2138–2145; Exhibit F: Results of the Metoprolol in Dilated Cardiomyopathy (MDC) Trial 342 Lancet 1441–1446 (1993), pp. 2146–2152; Exhibit G: Results of CIBIS I Trial 90 Circulation, 1765–1773 (1994), pp. 2153–2162; Exhibit H: Pfeffer editorial on U.S. Carvedilol Trials, 334 N.E.J. Med. 1396–1397 (1996), pp. 2163–2165;

Exhibit I: Results of COPERNICUS Trial, 344 N.E.J. Med. 1651–1658 (2001), pp. 2166–2174; Exhibit J: Results of BEST Trial, 334 N.E.J. Med. 1659–1667 (2001), pp. 2175–2184; Exhibit K: Further commentary on prior art, pp. 2185–2196; Exhibit T: Transcript of cross–examination of Dr. Parker taken on December 18, 2002, pp. 2197–2364, further including Exhibit 1: Johnstone et al., 10 Can J. Cardiol 613–631 (1994); Exhibit 2: Parker, 19 Eur. Heart J. Suppl. I 115–119 (1998); Exhibit 3: Rapaport et al., 101 Am. J. Med. 4A–61S–4A70S (1996); Exhibit 4: Al–Hesayen et al., 39 JACC 1269–1274 (2002); Exhibit 5: Azevedo et al., Circulation 2053–2056 (2000); Exhibit 6: Parker et al., 84 Circulation 1040–1048 (1991); Exhibit 7: Azevedo et al., 33 JACC 186–191 (1999); Exhibit 8: Azevedo et al., Circulation 274–279 (1999); Exhibit U: Affidavit of Dr. Ian Winterborn sworn Mar. 11, 2002, pp. 2365–2380, further including: Exhibit A: *Curriculum vitae*, pp. 2381–2385;

Exhibit B: Notice of Allegation (Nov. 28, 2001), pp. 2386–2406; Exhbit C: Notice of Application, pp. 2407–2423; Exhibit D: Canadian Letters Patent No. 2,212, 548, pp. 2424–2455; Exhibit E: Canadian Letters Patent No. 1,259,071, pp. 2456–2498; Exhibit F: Canadian Letters Patent No. 1,129,416, pp. 2499–2548; Exhibit G: United States Letters Patent No. 4,503,067, pp. 2549–2559.

Applicants' Record, vol. 6 of 7, filed in *Hoffmann–La Roche Limited, and Smithkline Beecham Corporation* v. *The Minister of Health, and Novopharm Limited*, Court No. T–84–02, containing an Index and: Exhibit V: Affidavit of Dr. Mitchell Arnold Henry Levine sworn Aug. 15, 2002, pp. 2560–2583, further including: Exhibit A: *Curriculum vitae*, pp. 2584–2614; Exhibit W: Transcript of cross–examination of Dr. Mitchell Arnold Henry Levine taken on Nov. 29, 2002, pp. 2615–2673, further including Exhibit A: Book entitled "Drugs of Choice: A Formulary for General Practice" (Canadian Medical Association: Toronto, 1995), pp. 2674–2849; Exhibit X: Affidavit of Dr. Michael Bohm sworn Aug. 16, 2002, pp. 2850–2875, further including Exhibit A: *Curriculum vitae*, pp. 2876–2980; Exhibit Y: Transcript of cross–examination of Dr. Michael Bohm taken on Dec. 9, 2002, pp. 2981–3028, further including:

Exhibit 1: Article entitled "Different Intrinsic Activities of Bucidolol, Carvedilol and Metoprolol in Human Failing Myocardium," British Journal of Pharmacology (2000), 130, 1131–1139, pp. 3029–3037; Exhibit 2: Article entitled "Prospective Crossover Comparison of Carvedilol and Metoprolol in Patients with Chronic Heart Failure," American College of Cardiology, 38(4), 934–46 (2001), pp. 3038–3045; Exhibit 3: "β–Blocker Treatment of Chronic Heart Failure with Special Regard to Carvedilol" from book entitled "Heart Rate is a Determinant of Cardiac Function—Basic Mechanism and Clinical Significance," G. Hasenfuss et al. ed. (Steinkopff Verlung Darmstadt 2000) pp. 3046–3067. Exhibit Z: Affidavit of Dr. Robert Rangno sworn Aug. 20, 2002, pp. 3068–3094, further including Exhibit A: *Curriculum vitae*, pp. 3095–3102. Exhibit AA: Transcript of cross–examination of Dr. Rangno taken on Nov. 15, 2002, pp. 3103–3152.

Affidavit of Dr. Mark Lautens filed in *GlaxoSmithKline Inc., and Smithkline Beecham Corporation* v. *The Minister of Health, and Apotex Inc.*, Court No. T–149–02, further including: Exhibit A: *Curriculum vitae*; Exhibit B: Dec. 12, 2001 Notice of Allegation from Apotex Inc. to Smithkline Beecham Pharma Inc.; Exhibit C: Canadian Letters Patent No. 1,259,071;

Notice of Application filed in *GlaxoSmithKline Inc., and Smithkline Beecham Corporation* v. *The Minister of Health, and Apotex Inc.*, Court No. T–149–02.

Record of the Respondent, Apotex Inc., filed in *GlaxoSmithKline Inc. and Smithkline Beecham Corporation* v. *The Minister of Health and Apotex Inc.*, Court File No. T–149–02, further including: Exhibit 1: Memorandum of Fact and Law of the Respondent, Apotex Inc.

Reasons for Order and Order, filed in *GlaxoSmithKline Inc. and Smithkline Beecham Corporation* v. *The Minister of Health and Pharmascience Inc.*, Court No. T–1871–01.

Amended Reasons for Order and Order, filed in *GlaxoSmithkline Inc. and Smithkline Beecham Corporation* v. *The Minister of Health and Pharmascience Inc.*, Court No. T–1871–01.

J. of Cardiovascular Pharm: DasGupta. et al., "The Effects of Intravenous Caredilol. A New Multiple Action Vasodilatory β–Blocker, in Cogestive Heart Failure" 1991, vol. 18, (Suppl 1): pp. S12–S16.*

J. of Cardiovascular Pharm; DasGupta et al., 1990 vol. 19, (Suppl. 1): pp. 562–567.*

Circulation; H. Krum et al., "Effects of Carvedilol, a Vasodilator–βBlocker in Patients with Congestive Heart Failure Due to Ishchemic Heart Disease". 1995, vol. 92, No. 2. pp. 212–218.*

CBS–TV; CBS Evenings News Transcript Jan. 27, 1993, 6:30–7:00 pm.*

CNBC; Steals and Deals, Transcript Jan. 29, 1993, 8:30pm.*

Circulation, DasGupta. et al., 1989, vol. 80, No. 4, (Suppl. II): pp. 116–117.*

Jan. 23, 2007 Office Action issued in U.S. Appl. No. 10/721,122, 7 pages.

As–filed Apr. 2, 2007, Response to Jan. 23, 2007, Office Action in U.S. Appl. No. 10/721,022, 68 pages.

Cleland et al., "Clinical trials update from the American College of Cardiology: darbepoetin alfa, Asteroid, Universe, paediatric carvedilol, Unload and Iceland," European Journal of Heart Failure, 8, pp. 326–329, 2006.

Shaddy et al., "The pediatric randomized carvedilol trial in children with chronic heart failure: Rationale and design," American Heart Journal, vol. 44, No. 3, pp. 383–389, Sep. 2002.

Summary Report, Study No.: SK&F–105517/321, "A Multicenter, placebo–controlled, 8–month study of the effect of twice daily carvedilol in children with congestive heart failure due to systemic ventricular systolic dysfunction," pp. 1–9, Jul. 2006.

Clinical Study Report, Study No.: SK&F–105517/321, "A Multicenter, placebo–controlled, 8–month study of the effect of twice daily carvedilol in children with congestive heart failure due to systolic dysfunction," abstract and cover pp. 1–4 and Clinical Study Report pp. 1–238, 266, 342–360, Jul. 17, 2006.

Summary Report, Study No.: SK&F–105517/396, "A Multicenter Open–label Extension Study to Evaluate the Safety of Twice Daily Oral Carvedilol in Pediatric Subjects with Chronic Heart Failure," abstract and cover pages pp. 1–4.

Clinical Study Report, Study No.: SK&F–105517/396, "A Multicenter Open–label Extension Study to Evaluate the Safety of Twice Daily Oral Carvedilol in Pediatric Sujects with Chronic Heart Failure," abstract and cover pages pp. 1–4 and Clinical Study Report pp. 1–135,, Aug. 2006.

J. of Cardiovascular Pharm; Senior, et al. "Effects of Carvedilol on Ventricular Arrhythmais", 1992, vol. 19, (Suppl). 1): pp: S117–S121.*

British J. of Urology; Caine, et al., "The Use of Alpha–adrenergic Blockers in Benign Prostatic Obstruction", 1976, vol. 48, pp. 255–263.*

British J. of Urology; H.N. Whitfield, et al., "The Effect of Adrenergic Blocking Drugs on Outflow Resistance", 1976, vol. 47, pp. 823–827.*

American J. of Cardiology; DasGupta, et al., "Value of Carvedilol in Congestive Heart Failure Secondary to Coronary Artery Disease", 1990, vol. 66, pp. 1118–1123.*

Z. Kardiol; A. Buchwald, et al., "Acute Hemodynamic Effects of the Beta–blocker Carvedilol in Heart Failure", 1990, vol. 79, No. 6, pp. 424–428.*

JACC; CiLenarda, et al., "Acute Hemodynamic Effects of Carvedilol Versus Metroprolol In Idiopathic Dilated Cardiomyopathy", 1991, vol. 17, No. 2, Abstract 142A.*

J. of Hypertension, C. Rosendorff, "Beta–blocking agents with vasodilator activity ", 1993, vol. 11, (Suppl. 4): pp. S37–S40.*

Cardiology; J. Lessem, et al., "Development of a Multication Beta–blocker", 1993, vol. 82, (Suppl. 3): pp. 50–58.*

Drug Safety; W.J. Louis, et al., "A Risk–Benefit Assessment of Carvedilol in the Treatment of Cardiovascular Disorders", 1994, vol. 11 No. 2, pp. 86–93.*

Drugs; McTavis, et al., "Carvedilol—A Review of its Pharmacodynamic and Pharmacokinetic Properties, and Therepeutic Efficacy", 1993, vol. 45, No. 2, pp. 232–258.*

Drugs of Today; Ruffolo, et al., "Carvedilol (Kredex): A Novel Multiple Action Cadiovascular Agent", 1991, vol. 27, No. 7, pp. 465–492.*

* cited by examiner

METHOD OF TREATMENT FOR DECREASING MORTALITY RESULTING FROM CONGESTIVE HEART FAILURE

Matter enclosed in heavy brackets [ ] appears in the original patent but forms no part of this reissue specification; matter printed in italics indicates the additions made by reissue.

FIELD OF THE INVENTION

The present invention relates to a new method of treatment using compounds which are dual non-selective β-adrenoceptor and $\alpha_1$-adrenoceptor antagonists, in particular the carbazolyl-(4)-oxypropanolamine compounds of Formula I, preferably carvedilol, for decreasing the mortality of patients suffering from congestive heart failure (CHF). The invention also relates to a method of treatment using compounds which are dual non-selective β-adrenoceptor and $\alpha_1$-adrenoceptor antagonists, in particular the carbazolyl-(4)-oxypropanolamine compounds of Formula I, preferably carvedilol, in conjunction with one or more other therapeutic agents, said agents being selected from the group consisting of angiotensin converting enzyme (ACE) inhibitors, diuretics, and digoxin, for decreasing the mortality of patients suffering from CHF.

BACKGROUND OF THE INVENTION

Congestive heart failure occurs as a result of impaired pumping capability of the heart and is associated with abnormal retention of water and sodium. Traditionally, treatment of chronic mild failure has included limitation of physical activity, restriction of salt intake, and the use of a diuretic. If these measures are not sufficient, digoxin, which is an agent that increases the force of mycardial contraction, is typically added to the treatment regiment. Subsequently, angiotensin converting enzyme inhibitors, which are compounds that prevent the conversion of angiotensin I into the pressor-active angiotensin II, are prescribed for chronic treatment of congestive heart failure, in conjunction with a diuretic, digoxin, or both.

Congestive heart failure is a condition that is associated with activation of both the renin-angiotenin system (RAS) and the sympathetic nervous system (SNS). Modulation of the RAS by angiotensin converting enzyme inhibitors has been shown to improve the symptoms associated with CHF. Sharpe, D. N., Murphy, J., Coxon, R. & Hannan S. F. (1984) Circulation, 70, 271–278. However, ACE inhibitors appear to have little effect on the enhanced SNS in CHF. Cohn, J. N., Johnson, G. & Ziesche, S., (1991) N. Engl. J. Med., 325, 293–302 and Francis, G. S., Rector, T. S. & Cohn, J. N. (1988) Am. Heart J., 116, 1464–1468. Therefore, there is a need for an agent that would be effective in blocking the activation of the SNS in CHF patients.

Also, congestive heart failure is a well-known cardiac disorder which results in an annual mortality in excess of 50 percent. Applefeld, M. M., (1986) Am. J. Med., 80, Suppl. 2B, 73–77. Therefore, therapeutic agents that would decrease the mortality resulting from CHF in patients suffering therefrom are highly desirable.

SUMMARY OF THE INVENTION

The present invention provides a new method of treatment using pharmaceutical compounds which are dual non-selective β-adrenoceptor and $\alpha_1$-adrenoceptor antagonists and, in particular, the carbazolyl-(4)-oxypropanolamine compounds of Formula I, alone or in conjunction with one or more other therapeutic agents, said agents being selected from the group consisting of ACE inhibitors, diuretics, and digoxin, as therapeutics for decreasing mortality resulting from congestive heart failure in mammals, particularly humans. In particular, the present invention preferably provides a method of treatment, alone or in conjunction with one or more other therapeutic agents, said agents being selected from the group consisting of ACE inhibitors, diuretics, and digoxin, for the compound of Formula I wherein $R_1$ is —H, $R_2$ is —H, $R_3$ is —H, $R_4$ is —H, X is O, Ar is phenyl, $R_5$ is ortho —$OCH_3$, and $R_6$ is —H, said compound being better known as carvedilol, which is (1-(carbazol-4-yloxy-3-[[2-(o-methoxyphenoxy)ethyl]amino]-2-propanol), or a pharmaceutically acceptable salt thereof.

DETAILED DESCRIPTION OF THE INVENTION

U.S. Pat. No. 4,503,067 discloses carbazolyl-(4)-oxypropanolamine compounds of Formula I:

(I)

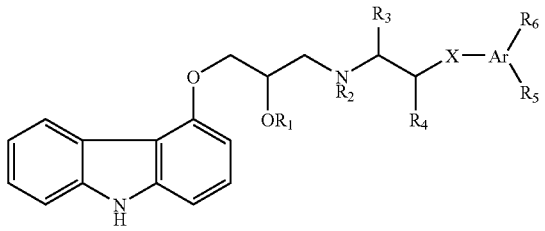

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

This patent further discloses a compound of Formula I, better known as carvedilol, which is (1-(carbazol-4-yloxy- 3-[[2-(o-methoxyphenoxy)ethyl]amino]-2-propanol), having the structure shown in Formula II:

(II)

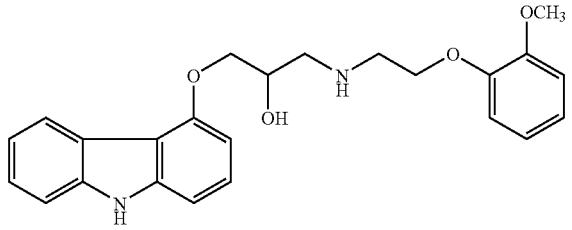

Formula I compounds, of which carvedilol is exemplary, are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $\alpha_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) Eur. J. Pharmacol., 176,237–240; Nichols, A. J., Gellai, M. & Ruffolo, R. R., Jr. (1991) Fundam. Clin. Pharmacol., 5, 25–38; Ruffolo, R. R., Jr., Gellai, M., Hieble, J. P., Willette, R. N. & Nichols, A. J. (1990) Eur. J. Clin. Pharmacol., 38, S82-S88; Ruffolo, R. R., Jr., Boyle, D. A., Venuti, R. P. & Lukas, M. A. (1991) Drugs of Today, 27, 465–492; and Yue, T.-L. Cheng, H., Lysko, P. G., Mckenna, P. J., Feuerstein, R., Gu. J., Lysko, K. A., Davis, L. L. & Feuerstein, G. (1992) J. Pharmacol. Exp. Ther., 263,92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble, J. P., Willette, R. N. & Nichols, A. J. (1990) Eur. J. Clin. Pharmacol., 38, S82-S88., Carvedilol also markedly reduces infarct size in rat, canine and porcine models of acute myocardial infarction. Ruffolo, R. R., Jr., et al., Drugs of Today, supra, possibly as a consequence of its antioxidant action in attenuating oxygen free radical-initiated lipid peroxidation, Yue, T.-L., et al. supra.

Recently, it has been discovered in clinical studies that pharmaceutical compounds which are dual non-selective β-adrenoceptor and $\alpha_1$-adrenoceptor antagonists, in particular the compounds of Formula I, preferably carvedilol, alone or in conjunction with conventional agents, said agents being ACE inhibitors, diuretics, and digoxin, are effective therapeutic agents for treating CHF. The use of agents, such as carvedilol in treating CHF is surprising, since, in general, β-blockers are contraindicated in patients suffering from heart failure, because β-blockers are known to have undesirable cardiodepressive effects. The most surprising observation from the studies in which the instant compounds were used to treat CHF is that said compounds, in particular carvedilol, are able to decrease the mortality resulting from CHF in humans by about 67 percent. Furthermore, this result is present across all classifications of CHF and both etiologies (eschemic and non-eschemic). This result is surprising since two recent mortality studies using the β-blockers metoprolol (Waagstein, et al., (1993) Lancet, 342, 1441–1446) and bisoprolol (CIBIS investigators and committees, (1994) Circulation, 90, 1765–1773) in the treatment of CHF showed no difference in mortality between drug-treated patients and placebo-treated patients.

According to the method of treatment of the present invention, the desirable therapeutic effect of the compounds of Formula I, particularly carvedilol, may be augmented by using any one of said compounds, or any pharmaceutically acceptable salt of said compounds. In conjunction with ACE inhibitors, diuretics, and digoxin, which are effective therapeutic agents for the treatment of CHF. In particular, the preferred ACE inhibitors of the present invention are selected from the group consisting of captopril, lisinopril, and enalapril, or any pharmaceutically acceptable salts thereof and the preferred diuretics of the present invention are hydrochlorothiazide or furosemide, or any pharmaceutically acceptable salts thereof. The desirable therapeutic benefits of the compounds of Formula I, particularly carvedilol, are additive with those of such ACE inhibitors, or diuretics, or digoxin when administered in combination therewith. Captopril is commercially available from E. R. Squibb & Sons, Inc. Lisinopril, enalapril and hydrochlorothiaxide are commercially available from Merck & Co. Furosemide is commercially available from Hoechst-Roussel Pharmaceuticals, Inc. Digoxin is commercially available from Burroughs Wellcome Co.

Compounds of Formula I may be conveniently prepared as described in U.S. Pat. No. 4,503,067. Carvedilol is commercially available from SmithKline Beecham Corporation and Boehringer Mannheim GmbH (Germany).

Pharmaceutical compositions of the compounds of Formula I, including carvedilol, alone or in combination with ACE inhibitors, or diuretics, or digoxin may be administered to patients according to the present invention in any medically acceptable manner, preferably orally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitored for well-known symptoms of intolerance, e.g., fainting, to such compound. Once the patient is found to tolerate such compound, the patient should be brought slowly and incrementally up to the maintenance dose. The preferred course of treatment is to start the patient on a dosage regimen of either 3.125 or 6.25 mg, preferably given twice daily, for two weeks. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for two more weeks, and observed for signs of intolerance. This course is continued until the patient is brought to a maintenance dose. The preferred maintenance dose is 25 mg, preferably given twice daily, for patients having a body weight of up to 85 kg. For patients having a body weight of over 85 kg, the maintenance dose is between about 25 mg and about 50 mg, preferably given twice daily; preferably about 50 mg, preferably given twice daily.

Dosing in humans for the treatment of disease according to the present invention includes the combination of compounds of Formula I with conventional agents. For example, the usual adult dosage of hydrochlorothiazide is 25–100 mg daily as a single dose or divided dose. The recommended starting dose for enalapril is 2.5 mg administered once or twice daily. The usual therapeutic dosing range for enalapril is 5–20 mg daily, given as a single dose or two divided doses. For most patients the usual initial daily dosage of captopril is 25 mg tid, with most patients having a satisfactory clinical improvement at 50 or 100 mg tid.

It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I, including the compound of Formula II, are used according to the present invention.

The example which follows is intended in no way to limit the scope of this invention, but is provided to illustrate how to use the compounds of this invention. Many other embodiments will be readily apparent to those skilled in the art.

EXPERIMENTAL

Mortality Studies in CHF Patients

Summary

To determine if β-adrenergic blockage might inhibit the deleterious effects of the sympathetic nervous system on survival in heart failure (CHF), 1052 patients with CHF were prospectively enrolled into a multicenter trial program, in which patients were randomly assigned (double-blind) to 6–12 months' treatment with placebo (PBO) or carvedilol (CRV).. After a common screening period, patients with class II–IV CHF (see next paragraph for the definitions of the classification of CHF) and an ejection fraction ≦0.35 were assigned to one of four protocols based on performance on a 6-minute walk test, PBO or CRV was added to existing therapy with digoxin, diuretics and an ACE inhibitor. All-cause mortality was monitored by a prospectively constituted Data and Safety Monitoring Board (DSMB). After 25 months of enrollment, the DSMB recommended termination of the program because of a favorable effect of CRV on survival. By intention-to-treat, mortality was 8.2% in the PBO group but only 2.9% in the CRV group (P=0.0001, Cochran-Mantel-Haensel analysis). This represented a reduction in risk of death by CRV of 67% (95% CI: 42% to 81%). The treatment effect was similar in patients with class II and class III–IV symptoms. Mortality was reduced in class II patients from 5.9% to 1.9%, a 68% reduction (95% CI: 20% to 97%) [P=0.015,], and in class III–IV patients from 11.0% to 4.2%, a 67% reduction (95% CI: 30% to 84%), [P=0.004, log-rank]. Importantly, the effect of CRV was similar in ischemic heart disease (risk reduced by 67%, P=0.003) and in non-ischemic dilated cardiomyopathy (risk reduced by 67%, P=0.014). In conclusion, the addition of CRV to conventional therapy is associated with a substantial (67%) reduction in the mortality of patients with chronic CHF. The treatment effect is seen across a broad range of severity and etiology of disease.

As used herein, by "Class II CHF" is meant patients with cardiac disease resulting in slight or moderate limitation of physical activity. They are comfortable at rest. Ordinary physical activity results in fatigue, palpitations, dyspnea, or anginal pain. By "Class III CHF" is meant patients with cardiac disease resulting in marked limitations of physical activity. They are comfortable at rest. Less than ordinary physical activity results in fatigue, palpitations, dyspnea, or anginal pain. By "Class IV CHF" is meant patients with cardiac disease resulting in inability to carry on any physical activity without discomfort, symptoms or cardiac insufficiency, or of the anginal syndrome. By "less than ordinary physical activity" is meant climbing one flight of stairs, or walking two hundred yards.

Design of Study

Patients on background therapy with diuretics, ACE inhibitors and/or digoxin were stratified on the basis of baseline submaximal exercise performance, into one of four trials:

study 220, a dose response study in moderate (NYHA II–IV) CHF with exercise testing as a primary endpoint study 221, a dose titration study in moderate (NYHA II–IV) CHF with exercise testing as a primary endpoint study 239, a dose titration study in severe (NYHA III–IV) CHF with quality of life as a primary endpoint study 240, a dose titration study in mild (NYHA II–III) CHF with progression of CHF as a primary endpoint Sixty-four centers in the US participated in the trial program. All sites conducted protocols 239 and 240, while 33 performed protocol 220 and 31 performed protocol 221.

Although each trial had its own individual objectives, the overall program objective defined prospectively was evaluation of all-cause mortality. Based upon a projected enrollment of 1100 patients, the program had 90% power to detect a 50% reduction in mortality (two-sided) between carvedilol and placebo, assuming a mortality rate in the placebo group of 12% over the duration of the trials ($\alpha$=0.05).

Randomization was preceded by a screening and challenge period common to the four protocols The purpose of the screening period was to qualify patients for study entry, obtain reproducible baseline measurements, and stratify patients into the appropriate trial based on submaximal exercise testing. During the challenge period, patients received low-dose open-label carvedilol (6.25 mg b.i.d.) for two weeks. Patients unable to tolerate this dose did not proceed to randomization. Patients tolerating low-dose carvedilol were then randomized to blinded medication (carvedilol or placebo) with the dose titrated over several weeks in the range of 6.25 to 50 mg b.i.d. (or equivalent level of placebo). The maintenance phase of each study ranged from six to 12 months, after which patients had the option of receiving open-label carvedilol in an extension study.

Results

The analysis presented below corresponds to the data set on which the DSMB made the recommendation to terminate the trials. Included in this intent-to-treat analysis are all patients enrolled in the U.S. trials as of Jan. 20, 1995; 624 receiving carvedilol and 356 placebo. An analysis of baseline patient characteristics (Table 1) shows good balance between the randomized groups.

TABLE 1

US Carvedilol Heart Failure Trials - Reaction Characteristics

| Characteristic | Placebo (n = 356) | Carvedilol (n = 624) |
|---|---|---|
| Age, mean ± SD (years) | 59.9 ± 11.7 | 58.8 ± 11.8 |
| Sex (% men) | 62% | 62% |
| Etiology (% ischemic) | 43% | 40% |
| Severity of CFP | | |
| Class II | 41% | 41% |
| Class III–IV | 40% | 39% |
| Unknown | 19% | 20% |
| LV ejection function, mean ± SD | 0.22 ± 0.07 | 0.25 ± 0.08 |
| 6 Minute walk (m ± SD) | 373 ± 88 | 379 ± 81 |
| Blood pressure (mmHg) | 115/73 | 115/73 |
| Heart rate (bpm ± SD) | 85 ± 13 | 86 ± 13 |

The overall mortality results for the program are shown in Table 2. All deaths that occurred during the intent-to-treat period are included. Treatment with caredilol resulted in a 67% reduction in the risk of all-cause mortality. Analysis of mortality by certain baseline characteristics shows this to be a broad effect regardless of severity or etiology of CHF. The effect was uniform in patients with mild heart failure or moderate to severe heart failure. Similarly, the mortality reduction was equivalent in patients with ischemic or non-ischemic heart failure.

TABLE 2

Evaluation of Mortality in US Carvedilol CHF Studies

| | Carvedilol | Placebo | Risk Reduction (95% CI) | p value[a] |
|---|---|---|---|---|
| All Cause Mortality | 18/624 (2.9%) | 29/356 (8.2%) | 67% (42–81) | <0.0001 |

TABLE 2-continued

Evaluation of Mortality in US Carvedilol CHF Studies

| | Carvedilol | Placebo | Risk Reduction (95% CI) | p value[a] |
|---|---|---|---|---|
| Class II CHF | 7/361 (1.9%) | 12/202 (5.9%) | 68% (20–97) | 0.015 |
| Class III–IV CHF | 11/263 (4.2%) | 17/154 (11.0%) | 66% (30–84) | 0.004 |
| Ischemic Etology | 10/311 (3.2%) | 16/178 (8.9%) | 67% (32–85) | 0.003 |
| Non-Ischemic Etiology | 8/313 (2.5%) | 13/178 (7.3%) | 67% (20–86) | 0.014 |

[a]Cochran-Mantal-Haeneal Analysis

Conclusion

The U.S. Phase III trials were prospectively designed to evaluate the effects of carvedilol on the wellbeing and survival of patients with congestive heart failure. Twenty-five months after the program was initiated, the independent Data and Safety Monitoring Board recommended that the trials be terminated because of a 67% reduction in all-cause mortality. This effect was independent of the underlying severity or etiology of heart failure.

The foregoing is illustrative of the use of the compounds of this invention. This invention, however, is not limited to the precise embodiment described herein, but encompasses all modifications within the scope of the claims which follow.

What is claimed is:

1. A method of decreasing mortality caused by congestive heart failure in a patient in need thereof which comprises administering a therapeutically acceptable amount of carvedilol in conjunction with one or more other therapeutic agents, said agents being selected from the group consisting of an angiotensin converting enzyme inhibitor (ACE), a diuretic, and digoxin,

*wherein the administering comprises administering to said patient daily maintenance dosages for a maintenance period to decrease a risk of mortality caused by congestive heart failure, and said maintenance period is greater than six months.*

2. A method according to claim 1 which comprises administering carvedilol in a dosage range of from about 3.125 to about 50 mg given twice daily.

3. A method according to claim 1 which comprises administering carvedilol in a maintenance dose of about 25 mg given twice daily.

4. A method according to claim 1 which comprises administering carvedilol in a maintenance dose of between about 25 mg and about 50 mg given twice daily to patients whose weight exceeds about 85 kg.

5. A method according to claim 1 which comprises administering carvedilol in a maintenance dose of about 50 mg given twice daily in patients whose weight exceed about 85 kg.

6. A method according to claim 1 wherein said ACE inhibitor is captopril, lisinopril, or enalapril, or any pharmaceutically acceptable salt thereof.

7. A method according to claim 1 wherein said diuretic is hydrochlorothiazide or furosemide, or any pharmaceutically acceptable salt thereof.

*8. A method according to claim 1, wherein the daily maintenance dosages and the maintenance period have been shown to statistically decrease the risk of mortality caused by congestive heart failure.*

*9. A method according to claim 1, wherein said patient has class II–IV congestive heart failure.*

* * * * *